United States Patent [19]

Boyd et al.

[11] Patent Number: 5,409,938
[45] Date of Patent: Apr. 25, 1995

[54] ANTIMALARIAL KORUPENSAMINES AND PHARMACEUTICAL COMPOSITIONS AND MEDICAL USES THEREOF

[75] Inventors: Michael R. Boyd, Ijamsville, Md.; Guido Francois, Oostende, Belgium; Gerhard Bringmann, Würzburg, Germany; Yaii F. Hallock, Ellicott City, Md.; Kirk P. Manfredi, Cedar Falls, Iowa; John H. Cardellina, II, Walkersville, Md.

[73] Assignee: The United States of America as represented by the Secretary, Department of Health and Human Services, Washington, D.C.

[21] Appl. No.: 195,260

[22] Filed: Feb. 14, 1994

[51] Int. Cl.$^6$ .................. A61K 31/47; C07D 217/02; C07D 217/04; C07D 217/06
[52] U.S. Cl. .................................... 514/307; 546/150
[58] Field of Search .................... 546/150; 514/307

[56] References Cited

U.S. PATENT DOCUMENTS 5,025,020 6/1991 Van Dyke ........................... 514/280
5,260,315 11/1993 Bringmann et al. ................. 514/307

OTHER PUBLICATIONS

Bringmann et al., "The absolute configuration of michellamine B, a 'dimeric', anti-HIV-active naphthylisoquinoline alkaloid," *Angew. Chem. (International Edition-English)*, 32, 1190–1191 (1993).
Bringmann et al., "The determination of the absolute configuration of N-methylated 1,3-dimethyltetrahydroisoquinolines by oxidative degradation," *Planta Med.*, 59 (supp.), A619–A620 (1993).
Bringmann et al., "Feeding deterrency and growth retarding activity of the naphthylisoquinoline alkaloid dioncophylline A against *spodoptera littoralis*," *Phytochemistry*, 31, 3821–3825 (1992).
Bringmann et al., "Ancistrobrevine B, the first naphthylisoquinoline alkaloid with a 5,8'-coupling site, and related compounds from *ancistrocladus abbreviatus*," *Phytochemistry*, 31, 4011–4014 (1992).
Bringmann et al., "Ancistobrevine D: An unusual alkaloid from *ancistrocladus abbreviatus*," *Planta Med.*, 58 (Supp. 1), A703–A704 (1992).
Bringmann et al., "A facile degradation procedure for determination of absolute configuration in 1,3-dimethyltetra- and dihydroisoquinolines," *Phytochemistry*, 30, 2067–2070 (1991).
Bringmann et al., "On the structure of these dioncophyllaceae alkaloids dioncophylline A (triphyophylline) and O-methyltriphyophylline," *Tetrahedron Lett.*, 31, 639–642 (1990).
Bringmann et al, "On the biosynthesis of acetogenic tetrahydrodroisoquinoline alkaloids: first *in vivo* feeding experiments," *Planta Med.*, 57 (supp. 2), A98 (1991).
Bringmann, "The Naphthyl Isoquinoline Alkaloids,"0 in *The Alkaloids*, vol. 29, (Brossi, ed.), Chapter 3, 141–184 (Academic Press, New York, 1986).
Chen et al., "Isolation and identification of the alkaloids from *ancistrocladus tectorius*," *Yao Hsueh Hsueh Pao (China)* (i.e., *Acta Pharmaceutica Sinica*), 16, 519–523 (1981).
Desjardins et al., "Quantitative assessment of antimalarial activity *in vitro* by a semiautomated microdilution technique," *Antimicrobial Agents Chemother.*, 16, 710–718 (1979).

(List continued on next page.)

Primary Examiner—Bernard Dentz
Attorney, Agent, or Firm—Leydig, Voit & Mayer, Ltd.

[57] ABSTRACT

The present invention provides new antimalarial compounds called korupensamines, korupensamine derivatives, and pharmacologically acceptable salts thereof, methods for isolating such antimalarial korupensamines from the plant *Ancistrocladus korupensis*, methods for obtaining new korupensamine derivatives, antimalarial compositions containing such antimalarial korupensamines or derivatives thereof or pharmacologically acceptable salts thereof, and methods of using such antimalarial compounds for the prevention of malaria infections or for treating mammals with malarial infections. The antimalarial compounds of the present invention inhibit the reproduction and cytopathicity of Plasmodium sp. parasites in vitro and in vivo.

41 Claims, 5 Drawing Sheets

OTHER PUBLICATIONS

Foucher et al., *Plantes Med. Phytother.*, 9, 87–98 (1975).

Grimm et al., "Deleterious effects of naphtylisoquinoline alkaloids on survival and growth of *spodoptera littoralis,*" *Planta Med.*, 58 (Sup. 1), 630 (1992).

Guinaudeau et al., "Bisbenzylisoquinoline alkaloids from *cyclea barbata,*" *J. Nat. Prod.*, 56 1989–1992 (1993).

Likhitwitayawuid et al., "Cyctotoxic and antimalarial bisbenzylisoquinoline alkaloids from *stephania erecta,*" *J. Nat. Prod.*, 56, 30–38 (1993).

Lin et al., "Cyctotoxic and antimalarial bisbenzylisoquinoline alkaloids from *cyclea barbata,*" *J. Nat. Prod.*, 56, 22–29 (1993).

Manfredi et al., "Novel alkaloids from the tropical plant *ancistrocladus abbreviatus* inhibit cell killing by HIV-1 and HIV-2," *J. Med. Chem.*, 34, 3402–3405 (1992).

Pavanand et al., "Antimalarial activity of *tiliacora triandra* dields against *plasmodium falciparum* in vitro," *Phytother. Res.*, 3, 215–217 (1989).

Ruangrungsi et al., "Traditional medicinal plants of Thailand, V. ancistrotectorine, a new naphthaleneisoquinoline alkaloid from *ancistrocladus tectorius,*" *J. Nat. Prod.*, 48, 529–535 (1985).

Sharma et al., "Alkaloids and terpenoids of *ancistorcladus heyneanus, sagittaria sagitifolia, lyonia formosa* and *hedychium spicatum,*" *Phytochemistry*, 14, 578–579 (1975).

Thomas et al., "*Ancistrocladus korupensis* (ancistroclasaceae): A new species of liana from Cameroon," *Novon*, 3 (4), 494–498 (1993).

Trager et al., "Human malarial parasites in continuous culture," *Science*, 193, 673–675 (1976).

Ye et al., "Selective antimalarial activity of tetrandine against chloroquinone resistant *plasmodium falciparum,*" *Biochem. Biophys. Res. Com.*, 159, 242–248 (1989).

KORUPENSAMINE A (1)

KORUPENSAMINE B (2)

KORUPENSAMINE C (3)

KORUPENSAMINE D (4)

ANCISTROBREVINE B

ANTIMALARIAL KORUPENSAMINES AND PHARMACEUTICAL COMPOSITIONS AND MEDICAL USES THEREOF

TECHNICAL FIELD OF THE INVENTION

The present invention relates to korupensamines and derivatives thereof which exhibit in vitro and in vivo antimalarial activity, methods for isolating substantially pure korupensamines from plants, methods for obtaining useful korupensamine derivatives, pharmaceutical compositions containing korupensamines or derivatives thereof, and methods for using the compounds for the treatment or prevention of malaria. The compounds of the present invention exhibit advantageous pharmacological, toxicological, or antimalarial properties, such as for example, inhibiting in vitro and in vivo the viability, growth, reproduction, and pathological effects of Plasmodia parasites, which are known to cause malaria.

BACKGROUND OF THE INVENTION

It is estimated that more than 2–3 million people die of malaria each year, and many more suffer from debilitating infection. Approximately a third of the world's population lives in malaria-endemic areas, including Central and South America, Asia, and Africa. Transient visitors or workers in these areas also are at ever-increasing risk of contracting malaria. Mosquitoes that carry malaria parasites have become resistant to insecticides, and the deadliest parasites have become resistant to previously effective antimalarial drugs such as chloroquine and other clinically used agents. New effective antimalarial chemotherapy agents are urgently needed. The present invention provides useful new antimalarial compounds and pharmaceutical compositions, as well as methods of using such antimalarial compounds and pharmaceutical compositions to prevent or treat malaria. These and other objects and advantages of the present invention, as well as additional inventive features, will be apparent from the description of the invention provided herein.

BRIEF SUMMARY OF THE INVENTION

The present invention is directed specifically to a new substantially pure compounds with antimalarial activity known as korupensamines A, B, C, and D, as well as pharmacologically acceptable salts thereof.

The present invention further provides a method of isolating the aforementioned korupensamines from a new species of the plant genus Ancistrocladus, named *Ancistrocladus korupensis*, which comprises the steps of:

(a) extracting dried Ancistrocladus korupensis plant material with an organic solvent to obtain a crude extract, (b) acid-base partitioning the crude extract to obtain a crude organic base fraction, (c) subjecting the crude organic base fraction to centrifugal partition chromatography, and (d) isolating the korupensamines with an amino-bonded phase HPLC column.

The present invention further includes a method of obtaining useful new antimalarial compounds by applying one or more well-known chemical reactions to a given korupensamine to obtain a korupensamine derivative wherein one or more phenolic hydroxyl group(s) may instead be replaced by an ester, sulfonate ester, or ether group; one or more methyl ether group(s) may instead be replaced by a phenolic hydroxyl group; one or more phenolic hydroxyl group(s) may instead be replaced by an aromatic hydrogen substituent; a secondary amine site may instead be replaced by an amide, sulfonamide, tertiary amine, or alkyl quaternary ammonium salt; a tertiary amine site may instead be replaced by a secondary amine; and one or more aromatic hydrogen substituent(s) may instead be replaced by a halogen, nitro, amino, hydroxyl, thiol, or cyano substituent.

The present invention therefore is directed more generally to the aforementioned substantially pure new korupensamines and derivative compounds, as well as pharmacologically acceptable salts thereof, with in vitro and in vivo antimalarial activity.

The present invention includes the aforementioned new antimalarial compounds, particularly korupensamines A, B, C, and D, their antimalarial derivatives, and pharmacologically acceptable salts thereof, in substantially pure form, as well as antimalarial compositions which comprise a pharmaceutically acceptable carrier and an antimalarial effective amount of at least one of these korupensamines or derivatives, or pharmacologically acceptable salts thereof. The antimalarial compositions can further include an antimalarial effective amount of chloroquine and/or other antimalarial agent(s), such as mefloquine, halofantrine, artemisinin, artemether, pyrimethamine, or quinine.

The present invention also encompasses a method of treating or preventing a malaria infection which comprises administering to a mammal in need thereof an antimalarial effective amount of at least one compound, or pharmacologically acceptable salt thereof, selected from the korupensamines, particularly korupensamines A, B, C, or D, or derivatives thereof. The method of the present invention may also involve co-administering an antimalarial effective amount of chloroquine or other antimalarial agent(s), such as mefloquine, halofantrine, artemisinin, artemether, or quinine, with at least one compound selected from the group consisting of the korupensamines, derivative compounds, and pharmacologically acceptable salts thereof.

BRIEF DESCRIPTION OF THE DRAWINGS

FIG. 4A shows the CD spectrum of korupensamine A (1) [---], compared with that of ancistrobrevine B [    x], while

DESCRIPTION OF THE PREFERRED EMBODIMENTS

Figure 1:
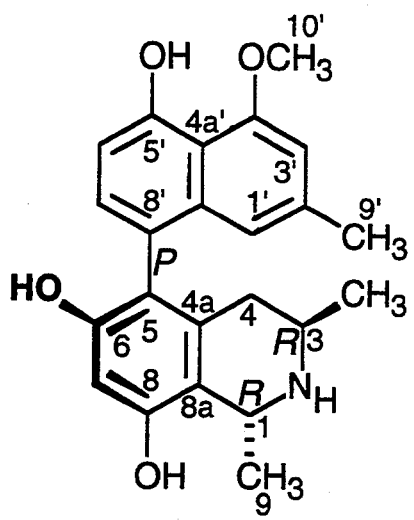
FIG. 1 illustrates the novel structures of antimalarial korupensamines A (1), B (2), C (3), and D (4).
Figure 1:
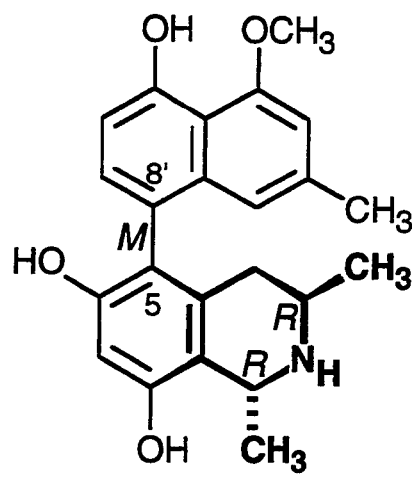
Figure 1:
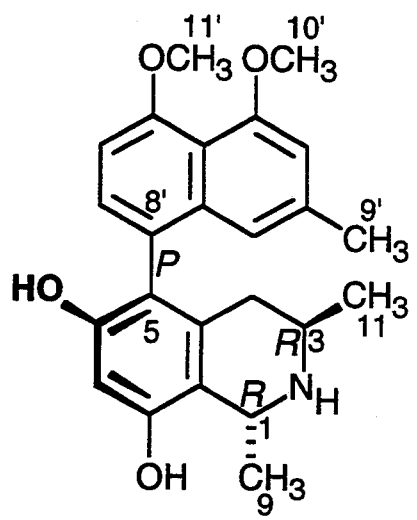
Figure 1:
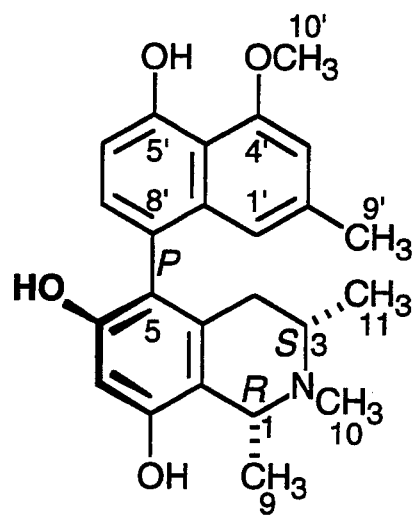

The present invention is predicated on the discovery that new compounds isolated from a recently identified new plant species of the genus Ancistrocladus, named *Ancistrocladus korupensis*, have in vitro and in vivo antimalarial properties, and therefore are useful for antimalarial treatments. The korupensamines, and derivatives thereof, of the present invention represent a distinct new class of compounds within the general type of compounds known as naphthylisoquinoline alkaloids.

Certain naphthylisoquinoline alkaloids, however not including any of the heretofore unknown korupensamines or derivatives thereof, have been known to occur in plant species of the Ancistrocladaceae and Dioncophyllaceae (e.g., see Bringmann, The Naphthylisoquinoline Alkaloids, in *The Alkaloids*, Vol. 29, Brossi, ed., Academic Press, New York, 1986, pp. 141-184). These small plant families occur in tropical Africa and southern and southeast Asia.

An arguably somewhat related class of naturally occurring compounds, called bisbenzylisoquinoline alkaloids, has been described; reportedly, some members of that class have in vitro antimalarial activity (Pavanand, et al., *Phytother. Res.*, 3, 215-217, 1989; Ye and VanDyke, *Biochem. Biophys Res. Commun.*, 159, 242-247, 1989; VanDyke, U.S. Pat. No. 5,025,020, 1991; Lin, et al., *J. Nat. Prod.*, 56, 22-29, 1993; Likhitwitayawuid, et al., *J. Nat. Prod.*, 56, 30-38, 1993; Guinaudeau, et al., *J. Nat. Prod.*, 56, 1989-1992, 1993). However, the latter chemical class is distinctly different from the korupensamines and derivatives of the present invention; moreover, no in vivo antimalarial activity of the bisbenzylisoquinoline alkaloid class is known; in fact it has been concluded by some authors (e.g., Likhitwitayawuid, et al., supra) that "bisbenzylisoquinoline alkaloids do not appear to be promising candidates as antimalarial agents."

The korupensamines and derivatives of the present invention are chemically unique in several respects. Their basic structure comprises a biaryl system consisting of a tetrahydrogenated isoquinoline moiety with an unprecedented methyl group at C-3. Moreover, these alkaloids display atropisomerism due to the bulky ortho-substituents adjacent to the biaryl axis (see FIG. 1). Such highly unusual structures presumably result from an unprecedented biogenetic origin, for which a polyketide pathway has been implicated (Bringmann, supra; Bringmann, et al., *Planta Med.*, 57, suppl. 2, 98-104, 1991). The korupensamines and derivatives of the present invention are unique among all heretofore known naphthylisoquinoline alkaloids in containing only one C-5 to C-8' linkage of a naphthalene and a tetrahydroisoquinoline group, an R configuration at C-1, and an exceptionally high polarity.

Several species from the Ancistrocladaceae and Dioncophyllaceae have been known to be used in the form of crude plant or extract preparations in folk medicine. For example, the roots of *Ancistrocladus tectorius* reportedly have been used for the treatment of malaria and dysentery (Bringmann, et al., *Tetrahedron Letters*, 31, 639-642, 1990), while other plants, such as *Triphyophyllum peltatum*, reportedly have been used to treat malaria and elephantiasis (e.g., see Ruangrungsi, et al., *J. Nat. Prod.*, 48, 529-535, 1985).

Some naphthylisoquinoline alkaloids in their pure forms had previously been reported to have noteworthy biological activities: ancistrocladidine (from *A. heyneanus*) had pronounced spasmolytic activity (Sharma, et al., *Phytochemistry*, 14, 578-583, 1975), and ancistrotectorine (from *A. tectorius*) had antitumor activity (Ruangrungsi, et al., supra). Dioncophyllines A and B were active as fungicides (Bringmann, et al., DE 41 17 080), and dioncophylline A had an antifeedant effect against the larvae of *Spodoptera littoralis* (Grimm, et al., *Planta Med.*, 58, Suppl. 1, 630, 1992; Bringmann, et al., *Phytochemistry*, 31, 3821-3825, 1992). However, no pure korupensamine or derivative thereof, nor any specific pharmaceutical composition thereof, had ever heretofore been provided, or shown to have antimalarial activity or to be useful for treatment or prevention of malaria.

The isolation and chemical identification of pure naphthylisoquinoline alkaloids, including ancistrocladeine (Foucher, et al., *Plantes Med. Phytother.*, 9, 26-29, 1975), ancistrocladine, hamatine, ancistrocline (Chen, et al., *Yaoxue Xuebao*, 16, 519-521, 1981; Bringmann, et al., *Planta Med.*, 58 (suppl. 1), 703-704, 1992) and ancistrotectorine (Ruangrungsi, et al., supra), had been reported from the stems, twigs, or leaves of *Ancistrocladus tectorius*. However, none of these compounds were known to have antimalarial activity, nor were they linked specifically to any antimalarial activity that (presumably) resided in these plants or extracts therefrom.

The present invention provides korupensamines and derivatives thereof, in substantially pure form, which exhibit such antimalarial activity, methods of isolating such korupensamines from native plants, methods of obtaining new korupensamine derivatives, pharmaceutical compositions containing such korupensamines or derivatives, and methods of treating or preventing malarial infections through the administration of such korupensamines or derivatives.

The specific korupensamine of interest has the formula:

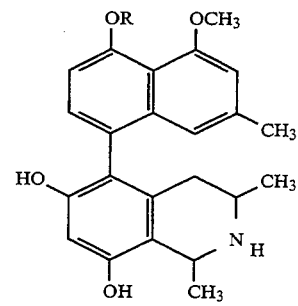

wherein R is either H or CH₃, particularly

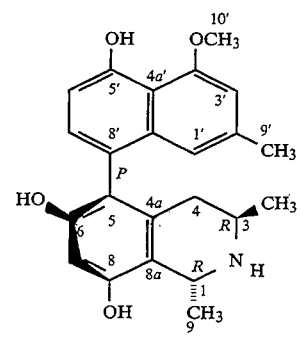

korupensamine A

-continued

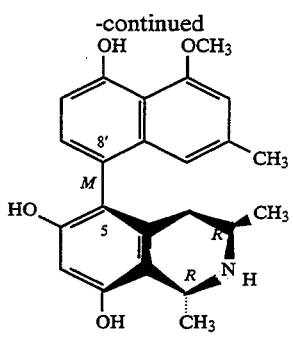

korupensamine B

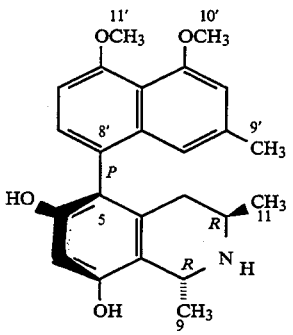

korupensamine C

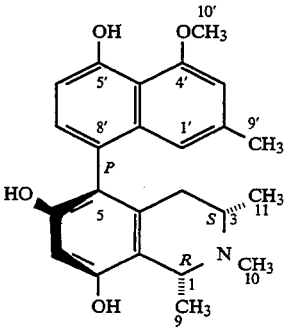

korupensamine D or is a pharmacologically acceptable salt thereof. The present invention provides such compounds in substantially pure form. The specific korupensamines are referred to herein as korupensamines A, B, C, and D, respectively, as indicated above and depicted in FIG. 1.

The present inventive method of isolating one of the aforementioned korupensamines, particularly korupensamine A, B, C, or D, from *Ancistrocladus korupensis* comprises (a) extracting dried plant material with an organic solvent to obtain a crude extract, (b) acid-base partitioning the crude extract to obtain a crude organic base fraction, (c) subjecting the crude organic base fraction to centrifugal partition chromatography, and (d) isolating the korupensamines with an amino-bonded phase HPLC column.

Certain chemical modification(s) can be introduced as desired into a given korupensamine to obtain a useful new derivative with modified biological properties such as: greater antimalarial potency against a particular Plasmodium sp., a broader spectrum of antimalarial activity against diverse Plasmodia sp., enhanced oral bioavailability, less toxicity in a particular host mammal, more advantageous pharmacokinetics and/or tissue distribution in a given host mammal, and the like. Therefore, the present invention additionally provides methods for obtaining useful new antimalarial compounds by applying one or more well-known chemical reactions to a given korupensamine to obtain a korupensamine derivative wherein one or more phenolic hydroxyl group(s) may instead be replaced by an ester, sulfonate ester, or ether group; one or more methyl ether group(s) may instead be replaced by a phenolic hydroxyl group; one or more phenolic hydroxyl group(s) may instead be replaced by an aromatic hydrogen substituent; a secondary amine site may instead be replaced by an amide, sulfonamide, tertiary amine, or alkyl quaternary ammonium salt; a tertiary amine site may instead be replaced by a secondary amine; and one or more aromatic hydrogen substituent(s) may instead be replaced by a halogen, nitro, amino, hydroxyl, thiol, or cyano substituent.

Accordingly, the present invention more generally provides a substantially pure new antimalarial korupensamine or derivative compound, or pharmacologically acceptable salt thereof, of

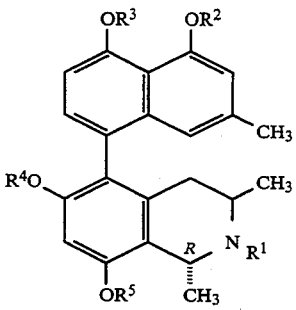

particularly a compound selected from the group consisting of:

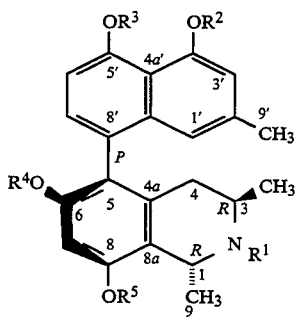

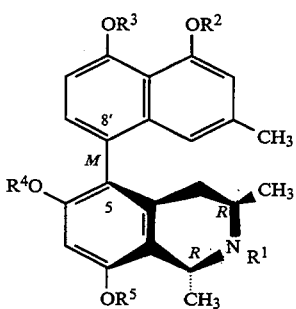

-continued

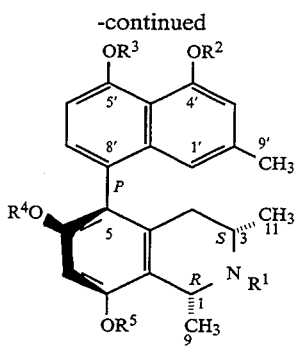

wherein $R^1$, $R^2$, $R^3$, $R^4$ and $R^5$ are the same or different and are each H, $C_1$-$C_6$ alkyl, $R^6CH_2$—, $R^6CO$—, $R^6SO_2$—, wherein $R^6$ is $C_1$-$C_6$ alkyl or aryl, and one or more ring positions at 1', 3', 4', 5', 6', 7', 6, 7, or 8 may instead be a halogen, nitro, amino, hydroxyl, thiol, or cyano substituent.

A pharmaceutical composition of the present invention is an antimalarial composition which comprises a pharmaceutically acceptable carrier and an antimalarial effective amount of at least one of the aforementioned korupensamines, particularly korupensamine A, B, C, or D or derivative thereof, or a pharmacologically acceptable salt thereof.

The present inventive compositions may include other active or inactive components. In particular, they may include other antimalarial agents such as an antimalarial effective amount of chloroquine, mefloquine, halofantrine, artemisinin, artemether, pyrimethamine, quinine, or other antimalarial agents.

The korupensamines, korupensamine derivatives, and salts thereof can be used for a variety of in vitro purposes, particularly in assays and the like. These compounds can also be used for in vivo purposes, particularly to prevent and/or treat malarial infections.

The present inventive method of treating or preventing a malarial infection comprises administering to a mammal in need thereof an antimalarial effective amount of at least one of the aforementioned korupensamines, particularly korupensamine A, B, C, or D or korupensamine derivative, or a pharmacologically acceptable salt thereof. The treatment method may involve the use of the aforementioned antimalarial compositions, and, thus, the treatment method may involve the use of pharmaceutically acceptable carriers and the coadministration of other active or inactive components, in particular, other antimalarial agents such as an antimalarial effective amount of chloroquine, mefloquine, halofantrine, artemisinin, artemether, pyrimethamine, quinine, or other antimalarial agents. The particular infecting malaria-causing organism may be any responsible pathogenic parasite, particularly such as a Plasmodium sp., more particularly such as *P. falciparum*, *P. vivax*, *P. malariae*, *P. ovale*, or *P. berghei*.

Definitions

The pharmacologically acceptable salt may be any such suitable salt. Examples of pharmacologically acceptable salts include HBr, HCl, oxalate, citrate, acetate, tartrate, and the like.

By $C_1$-$C_6$ alkyl is meant straight or branched chain $C_1$-$C_6$ alkyl groups. Examples include, but are not limited to, methyl, ethyl, n-propyl, iso-propyl, n-butyl, iso-butyl, sec-butyl, tertiary-butyl, n-pentyl, iso-pentyl, and n-hexyl.

By aryl is meant an organic radical derived from an aromatic hydrocarbon. Examples of an aryl group include phenyl and o-, m-, and p-hydroxyphenyl.

By aliphatic is meant organic radical derived from an open hydrocarbon chain. Examples of aliphatic radicals include alkanes, alkenes, and alkynes. Specific examples of aliphatic radicals which can be used in the present invention include, but are not limited to, $C_1$-$C_6$ alkyl radicals, straight or branched. *Ancistrocladus korupensis*

The compounds (FIG. 1) of the present invention are isolated from a newly identified plant species of the genus Ancistrocladus, named *Ancistrocladus korupensis*, from which related "dimeric" naphthylisoquinoline alkaloids, called michellamines, were originally isolated (Manfredi, et al., *J. Med. Chem.*, 34, 3402–3405, 1992). A preliminary communication (Manfredi et al., supra) initially named the michellamine-containing plant (which is also the same plant from which the korupensamines of the present invention are isolated) as *Ancistrocladus abbreviatus* (See also U.S. patent application Ser. No. 07/684,197, filed Apr. 12, 1991, now abandoned, and PCT/US92/02805). However, subsequently it became clear that *A. abbreviatus* was actually devoid of michellamines (and now korupensamines) and that the true michellamine-containing (and now korupensamine-containing) plant species, while having many similarities to *A. abbreviatus*, was an Ancistrocladus species previously unknown to science (see U.S. patent application Ser. No. 08/049,824, filed Apr. 19, 1993, and PCT/US93/03682). The source plant is now officially known as *Ancistrocladus korupensis* (D. W. Thomas and Gereau, *Novon*, 3, 494–498, 1993).

The Ancistrocladaceae is a small paleotropical family in the order Theales, with about 20 species known from Asia and tropical Africa. So far, ten species have been described from Africa. *Ancistrocladus korupensis*, presently the only known natural source of michellamines (and now korupensamines), differs from all previously described African species of Ancistrocladus in having petals slightly shorter than the sepals; the petals are about twice as long as the sepals in other species (U.S. patent application Ser. No. 08/049,824, supra). The original voucher specimen of the plant was collected (collection #6889) on Mar. 25, 1987 by Duncan Thomas (DT) in the Korup National Park, west of Mundemba Town in Cameroon's Southwest Province (5°01'N; 8°51'E, 60 m elevation above sea level). A sample of the voucher specimen of *Ancistrocladus korupensis* (DT 6889) is preserved in the herbarium of the Missouri Botanical Garden, where it is available for viewing by the public.

Isolation of the korupensamines from plant extracts

A variety of methods can be used to isolate the korupensamines. Among these methods are extraction, solvent-solvent partitioning, centrifugal partition chromatography, gel permeation chromatography, and HPLC with a variety of bonded phases. The isolation of the compounds can be monitored by UV, TLC, and antimalarial bioassay.

The procedure described herein is of a scale to accommodate an initial starting amount of approximately ½ kilogram of the air-dried plant material consisting of leaves, stems, and twigs. This plant material is first ground to a coarse powder and extracted with 1:1 MeOH:$CH_2Cl_2$, followed by a second extraction with methanol. These initial crude organic extracts typically amount to a total of approximately 8–10% of the mass of the original dried plant material. This crude extract then is dissolved in 5% aqueous HCl and extracted with $CHCl_3$. The aqueous layer is made basic with concentrated $NH_4OH$ to a pH of 10–11; it is then extracted with 4:1 $CHCl_3$:MeOH followed by 1:1 MeOH:$CHCl_3$ to give a total of about 0.5–1.0 g of basic extract after removal of the solvent. The extract is then dissolved in the lower phase of a 5:5:3 ($CHCl_3$:MeOH:0.5% aqueous HBr) biphasic solvent system and fractionated on a Sanki CPC operating in the descending mode. The effluent is monitored at 254 nm. After removal of the solvent, korupensamine-containing fractions typically comprise a total mass of about 200–400 mg. The mixture is further separated with amino-bonded phase HPLC using 43:7 $CHCl_3$:MeOH/0.075% $(NH_4)_2CO_3$ as the solvent. Using this general procedure, the overall yield of korupensamines from crude organic extract is about 3% for korupensamine A, 2% for korupensamine B, 0.1% for korupensamine C, and 0.04% for korupensamine D.

EXAMPLES

The following examples further illustrate the present invention but, of course, should not be construed as in any way limiting its scope.

Example 1

This example more specifically illustrates the isolation of antimalarial korupensamines from the plant species *Ancistrocladus korupensis*. The in vitro and in vivo antimalarial activities of the isolated korupensamines can be demonstrated as in Example 5.

The leaves and stems of dried *Ancistrocladus korupensis* (449 g) were ground in a Wiley mill and extracted with 1:1 MeOH—$CH_2Cl_2$ in a Kimax percolator. The ground material was allowed to steep in the solvent overnight. The solvent was removed by filtration and evaporated at reduced pressure to give 36.62 g of crude organic extract.

A portion (3.438 g) of this extract was suspended/dissolved in 200 ml of 5% aqueous HCl and extracted with five 80 ml aliquots of $CHCl_3$. The aqueous phase was adjusted to pH=10 with concentrated $NH_4OH$ and extracted with $CHCl_3$—MeOH (1:1; 8×100 ml). The extracts were combined and the solvent removed at reduced pressure to give 0.907 g of residue. This residue was fractionated on a Sanki centrifugal partition chromatograph using the lower phase of a $CHCl_3$—MeOH—0.5% HBr (5:5:3) mixture as the mobile phase (2.8 ml/min, 400 rpm) and monitoring at 254 nm. The korupensamines eluted in middle fractions, while the dimeric michellamines appeared in later fractions. Repeated HPLC (Rainin Dynamax $NH_2$, 2.1×25 cm) of those middle fractions with $CH_2Cl_2$—MeOH/0.075% ammonium carbonate (19:1) afforded pure korupensamine A (1) (110 mg, 3.1% of the crude extract), korupensamine B (2) (64 mg, 1.8% of the crude extract), korupensamine C (3) (4.9 mg, 0.1% of the crude extract), korupensamine D (4) (2.7 mg, 0.04% of the crude extract).

Example 2

This example sets forth information defining the chemical structures of the korupensamines isolated in accordance with Example 1. The structures and relative stereochemistry were solved from the NMR, NOE, and HMBC data (Tables 1–4).

TABLE 1

| Position | 500 MHz $^1$H NMR data of 1, 2, 3, and 4: δ (mult. J in Hz) | | | |
|---|---|---|---|---|
| | 1 | 2 | 3 | 4 |
| 1 | 4.35(q, 6.5) | 4.37(q, 6.5) | 4.44(q, 6.8) | 3.73(q, 6.4) |
| 3 | 3.13(m) | 3.13(m) | 3.23(m) | 2.26(m) |
| 4Hax | 1.73(dd, 10.5, 17) | 2.04(dd, 12, 17) | 1.79(dd, 11.3, 17) | 2.20(dd, 10.5, 15.6) |
| 4Heq | 2.24(dd, 4, 17) | 1.93(dd, 4.5, 17) | 2.29(dd, 4.5, 17) | 1.87(dd, 2, 15.6) |
| 5 | — | — | — | — |
| 7 | 6.33(s) | 6.33(s) | 6.35(d) | 6.32(s) |
| 1' | 6.71(br s) | 6.81(br, s) | 6.74(d, 2.0) | 6.75(d, 1.5) |
| 3' | 6.75(br s) | 6.77(br, a) | 6.71(d, 2.0) | 6.77(d, 1.5) |
| 6' | 6.77(d, 8.0) | 6.76(d, 8.0) | 6.92(d, 8.0) | 6.76(d, 7.8) |
| 7' | 7.07(d, 8.0) | 7.02(d, 8.0) | 7.13(d, 8.0) | 7.08(d, 7.8) |
| C1-Me | 1.44(d, 6.5) | 1.49(d, 6.5) | 1.40(d, 6.8) | 1.47(d, 6.4) |
| C3-Me | 0.92(d, 6.5) | 0.99(d, 6.5) | 0.97(d, 6.4) | 0.96(d, 6.4) |
| C2'-Me | 2.27(s) | 2.32(s) | 2.28(s) | 2.31(s) |
| N-Me | — | — | — | 2.41(s) |
| C6-OMe | — | — | — | — |
| C4'-OMe | 4.01(s) | 4.07(s) | 3.91(s) | 4.07(s) |
| C5'-OMe | — | — | 3.94(s) | — |

TABLE 2

| Position | Mult.$^a$ | 125 MHz $^{13}$C NMR data for 1, 2, 3, and 4 | | | |
|---|---|---|---|---|---|
| | | 1 | 2 | 3 | 4 |
| 1 | d | 48.48 | 48.32 | 48.70 | 59.23 |
| 2 | — | — | — | — | — |
| 3 | d | 43.13 | 43.60 | 43.49 | 56.98 |
| 4 | t | 35.64 | 35.58 | 35.23 | 37.52 |
| 4a | s | 135.83 | 135.76 | 135.35 | 137.39 |
| 5 | s | 119.03 | 118.93$^b$ | 119.32 | 118.42 |
| 6 | s | 155.00 | 155.10$^c$ | 155.31$^b$ | 154.65$^b$ |
| 7 | d | 101.24 | 101.41 | 101.43 | 101.64 |
| 8 | s | 155.18 | 155.27$^c$ | 155.43 | 155.35$^b$ |
| 8a | s | 118.55 | 118.88$^b$ | 117.69$^c$ | 119.29 |
| 1' | d | 119.50 | 119.36 | 118.89 | 119.60 |
| 2' | s | 136.94 | 137.11$^d$ | 137.41 | 137.02 |
| 3' | d | 107.31 | 107.41 | 109.89 | 107.38 |
| 4' | s | 157.70 | 157.80 | 158.55 | 157.80 |
| 4a' | s | 114.83 | 114.86 | 117.58$^c$ | 114.76 |
| 5' | s | 155.30 | 155.43 | 157.88 | 155.31 |
| 6' | d | 110.22 | 110.31 | 106.89 | 110.24 |
| 7' | d | 131.12 | 131.61 | 130.17 | 131.87 |
| 8' | s | 125.78 | 125.83 | 127.74 | 125.79 |
| 8a' | s | 137.35 | 137.26$^d$ | 138.05 | 137.22 |
| C1-Me | q | 20.49 | 20.22 | 20.21 | 21.77 |
| C3-Me | q | 21.76 | 21.82 | 21.40 | 20.59 |
| C2'-Me | q | 22.04 | 22.23 | 21.99 | 22.18 |
| N-Me | q | — | — | — | 41.34 |
| C6-OMe | q | — | — | — | — |
| C4'-OMe | q | 56.64 | 56.71 | 56.98 | 56.72 |

TABLE 2-continued

| | 125 MHz $^{13}$C NMR data for 1, 2, 3, and 4 | | | | |
|---|---|---|---|---|---|
| Position | Mult.[a] | 1 | 2 | 3 | 4 |
| C5'-OMe | q | — | — | 56.79 | — |

[a]Determined by DEPT experiments. Assignments are based on HMQC and HMBC correlations.
[b,c,d]Assignments may be interchanged.

TABLE 3

| | NOE correlations[a] observed for 1, 2, 3, and 4 | | | |
|---|---|---|---|---|
| Proton | 1 | 2 | 3 | 4 |
| H1 | 9 | 9 | 9 | 3, 9, 10 |
| H3 | 4eq, 9, 11 | 4eq, 9, 11 | 4eq, 9, 11 | 1, 4eq, 10, 11 |
| H4ax | 4eq, 11, 1' | 4eq, 11, 7' | 4eq, 11, 1' | 4eq, 11, 7' |
| H4eq | 3, 4ax, 7' | 3, 4ax, 11, 1' | 3, 4eq, 7' | e, 4ax, 11, 1' |
| H5 | — | — | — | — |
| H7 | — | — | — | — |
| H9 | 1, 3 | 1, 3 | 1, 3 | 1, 10 |
| H10 | — | — | — | 1, 3, 9, 11 |
| H11 | 3, 4ax | 3, 4eq, 4ax | 3, 4ax | 3, 4ax, 4eq, 10 |
| H12 | — | — | — | — |
| H1' | 4ax, 9' | 4eq, 9' | 4ax, 9' | 4eq, 9' |
| H3' | 9', 10' | 9', 10' | 9', 10' | 9', 10' |
| H6' | 7' | 7' | 7', 11' | 7' |
| H7' | 4eq, 6' | 4ax, 6' | 4eq, 6' | 4ax, 6' |
| H9' | 1', 3' | 1', 3' | 1', 3' | 1', 3' |
| H10' | 3' | 3' | 3' | 3' |
| H11' | — | — | 6' | — |

[a]Numbers refer to protons which show NOE correlations to those listed.

TABLE 4

| | HMBC correlations[a] for 1, 2, 3, and 4 | | | |
|---|---|---|---|---|
| Position[b] | | | | |
| C1 | 9 | 3, 9 | 9 | 9, 10 |
| C3 | 1, 4, 11 | 1, 4, 11 | 1, 4, 11 | 4, 10, 11 |
| C4 | 11 | 11 | 11 | 11 |
| C4a | 1, 4 | 1, 3, 4 | 1, 4 | 1, 3, 4 |
| C5 | 4, 7, 7' | 4, 7, 7' | 4, 7, 79 | 4, 7, 7' |
| C6 | 7 | 7 | 7 | 7 |
| C7 | — | — | — | — |
| C8 | 1, 4, 7, 9 | 1, 4, 7, 9 | 1, 4, 7, 9 | 1, 4, 7, 9 |
| C9 | 1 | 1 | 1 | 1 |
| C10 | — | — | — | 1 |
| C11 | 4 | 4 | 4 | 4 |
| C12 | — | — | — | — |
| C13 | 3', 9' | 3', 9' | 3', 9' | 3', 9' |
| C2' | 9' | 9' | 9' | 9' |
| C3' | 1', 9' | 1', 9' | 1', 9' | 1', 9' |
| C4' | 10' | 10' | 10' | 10' |
| C4a' | 1', 3', 6' | 1', 3', 6 | 1', 3', 6 | 1', 3', 61 |
| C5' | 6', 7' | 6', 7' | 6', 7', 11' | 6', 7' |
| C6' | — | — | 7' | — |
| C7' | — | — | — | — |
| C8' | 1', 6' | 1', 6' | 6' | 6' |
| C8a' | 1', 7' | 7' | 7' | 7' |
| C9' | 1', 3' | 1', 3' | 1', 3' | 1', 3' |

[a]Measured on 500 MHz with $J_{xn} = 8.2$ Hz,
[b]Carbons to which correlations were observed.

Figure 2:
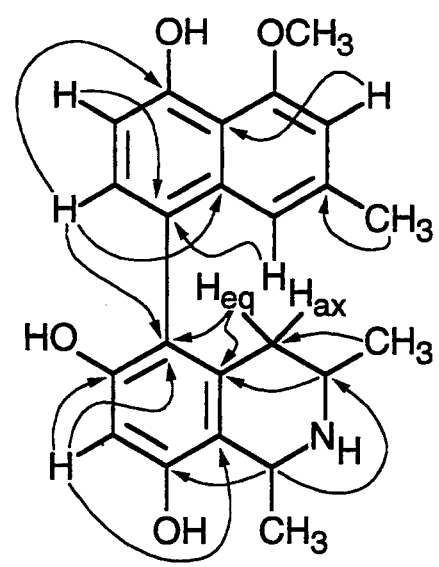
FIG. 2 shows selected HMBC correlations of korupensamine A (1).
Figure 3:
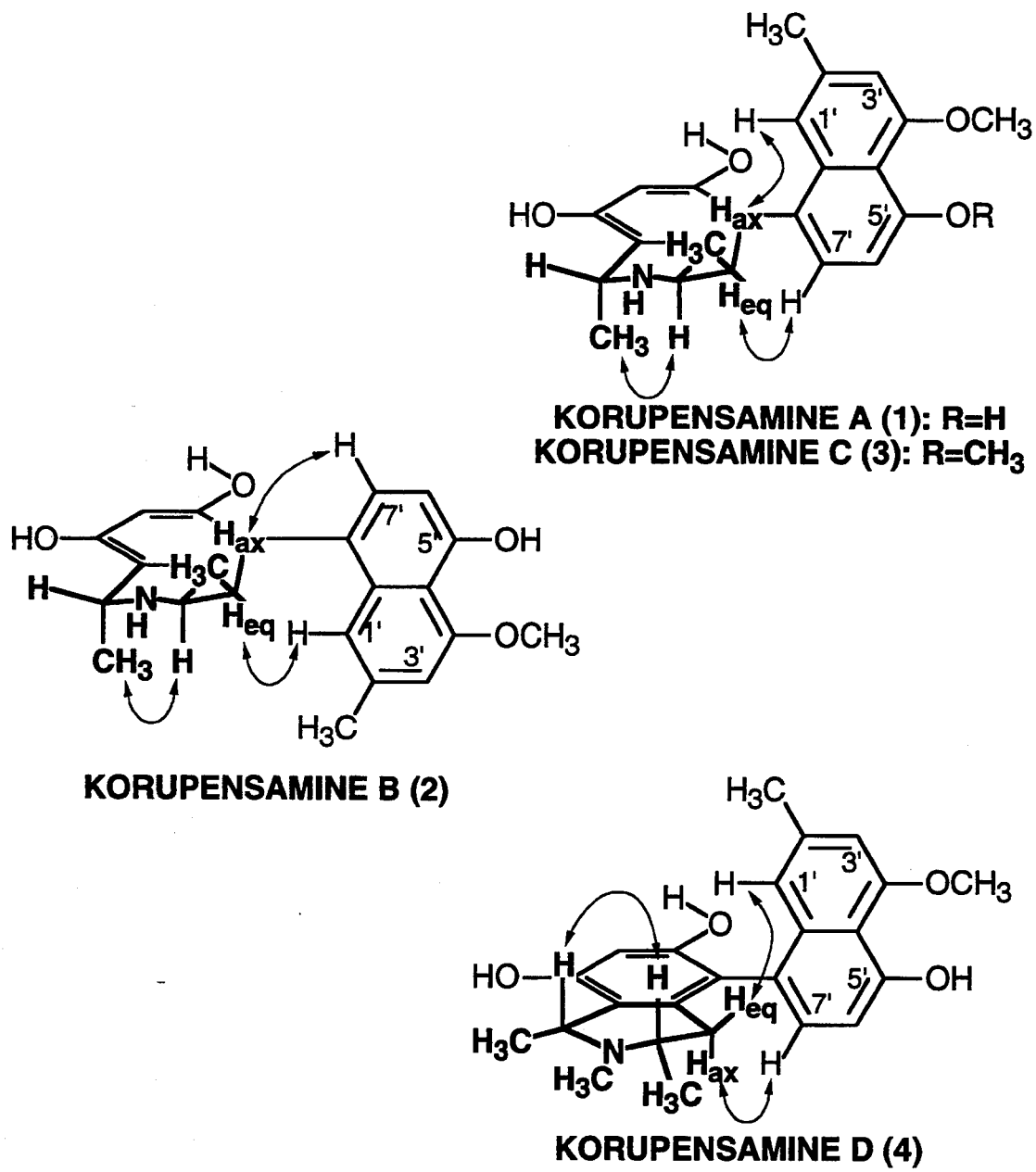
FIG. 3 depicts the key NOE interactions of korupensamines A (1), B (2), C (3), and D (4) for the elucidation of relative configurations of centers and axes.
Figure 4A:
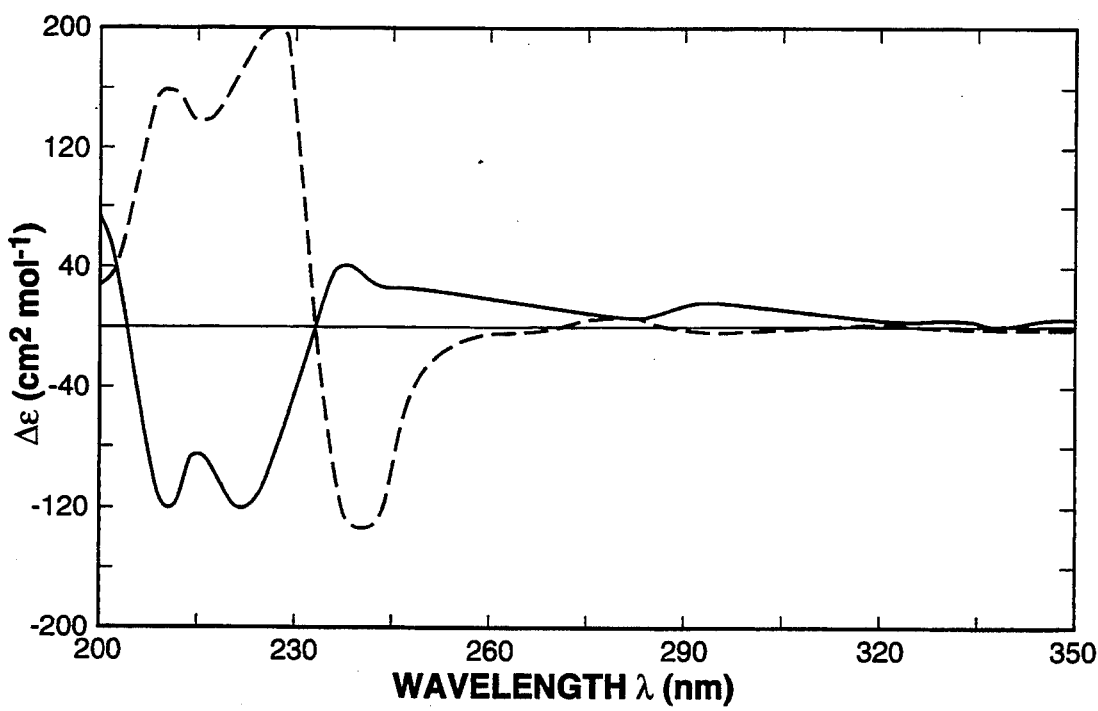
Figure 4B:
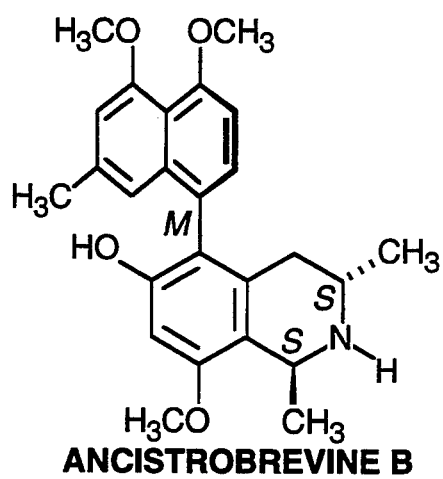
FIG. 4B depicts the structure of ancistrobrevine B.

Korupensamine A (1) was isolated as an optically active light tan solid, which gave a HREIMS molecular ion at m/z 379.1787, indicating a molecular formula of $C_{23}H_{25}NO_4$. The $^{13}$C NMR spectrum (DEPT) disclosed the presence of four methyl, one methylene and seven methine resonances. The $^1$H NMR spectrum contained two methyl doublets (δ1.44 and 0.92) and two methyl singlets (δ2.27 and 4.01). Additional proton signals included a methylene (δ1.73 and 2.24) and two methines (δ3.13 and 4.35). The aromatic region of the proton spectrum contained a singlet and two pairs of coupled protons, in ortho and meta relationships, respectively. These data suggested that korupensamine A was a new member of the general naphthylisoquinoline alkaloid class well known from the family Ancistrocladaceae (see, e.g., Bringmann, supra). One-bond and long-range, proton-detected heteronuclear correlation experiments (HMQC and HMBC, see FIG. 2) allowed the complete assignment of the $^1$H and $^{13}$C spectral data and established the substitution patterns on both the naphthalene and tetrahydroisoquinoline ring systems. Further, HMBC data revealed that the two units were connected at C5 and C8' (FIG. 2), an uncommon linkage in this family. The C5 carbon showed correlations to protons H7' (δ7.07), H7 (δ6.33), and H4 (δ1.73 and 2.24). Only the michellamines (Manfredi, et al., supra) and ancistrobrevine B (see FIG. 4B) (Bringmann, et al., Phytochemistry, 31, 4011–4014, 1992) have previously been found to have those points of connection (Bringmann, et al., supra), Difference NOE experiments (FIG. 3) established the relative stereochemistry of korupensamine A (1) in the tetrahydroisoquinoline ring. Irradiation of the H3 signal elicited a strong NOE on the C3-methyl and a moderate NOE on the C1-methyl, suggesting a 1,3-diaxial disposition of the H3 and C1-methyl protons. The coupling constants between H3 and the two H4 protons (4.0, 11.5 Hz) indicated a trans-diaxial relationship between the signal at δ1.73 (H4ax) and H3, thus placing the other H4 proton (δ2.24) in the equatorial position. This assignment was supported by the NOE observed between H4eq and H3 (FIG. 3). The NOE between the H4 methylene protons and the aromatic protons H1' and H7' proved to be the key for the determination of the relative stereochemistry around the atropic axis C5-C8'. The H4eq proton (δ2.24) showed a moderate NOE on H7' while irradiation of H4ax (δ1.73) gave an enhancement of the H1' signal at δ6.71. This information suggested that the tetrahydroisoquinoline ring system was essentially orthogonal to the naphthylene ring system plane. Other physicochemical and spectral data for korupensamine A are as follows: [α]$_D$ −75.5° (c 1.84, MeOH); UV λ$_{max}$ (MeOH): 230 nm (log ε4.6), 290 (3.8), 307 (3.8), 323 (3.8), 338 (3.8); IR (film) ν$_{max}$ 3400, 3000, 1615, 1585 cm$^{-1}$; HREIMS: obsd m/z 379.1787 (calc'd for $C_{23}H_{25}NO_4$, 379.1783).

Korupensamine B (2) was also an optically active tan solid, and possessed the molecular formula of $C_{23}H_{25}NO_4$ from HREIMS analysis. The $^1$H and $^{13}$C NMR spectra markedly resembled those of korupensamine A (1), suggesting that korupensamine B (2) was isomeric to korupensamine A (1). The UV spectra of korupensamine B (2) and korupensamine A (1) were practically superimposable. Most notable was the observation that the 1H NMR signals for the methylene at C-4 were different from those of korupensamine A (1). The slightly more downfield signal (δ2.04) was in an axial disposition as indicated by the coupling constants (J=12, 17Hz). Unlike the case of korupensamine A (1), irradiation of this signal in an NOE experiment gave a strong enhancement of H7'. The other proton at C-4 (δ1.93) was in an equatorial orientation (J=4.5, 17 Hz) and showed an NOE relationship with the H1' signal, as shown in FIG. 3. Further NOE experiments revealed that the relative stereochemistry around the nitrogen-containing ring (C1 and C3) was identical to that of korupensamine A (1). This compound, therefore, was assigned as the C5-C8' atropisomer of korupensamine A (1). Other physicochemical and spectral data for korupensamine B include the following: [α]$_D$+65° (c 0.76, MeOH); UV λ$_{max}$(MeOH): 230 nm (log ε4.5), 290 (3.7), 308 (3.8), 323 (3.7), 337 (3.7); IR (film) ν$_{max}$ 3400, 3000, 1615, 1585 cm$^{-1}$; HREIMS obsd m/z 379.1758 (calc'd for C$_{23}$H$_{25}$NO$_4$, 379.1783).

Korupensamine C (3) gave a parent ion at m/z 393.1975 by HREIMS, corresponding to a molecular formula of C$_{24}$H$_{27}$NO$_4$. The presence of a methoxyl group in place of a phenolic OH was evident from a sharp singlet at δ3.94 in the $^1$H NMR spectrum and a new carbon signal at 56.79 in the $^{13}$C NMR spectrum. The remaining $^1$H and $^{13}$C signals for korupensamine C (3) were very similar to those recorded for korupensamine A (1). The location of the new O-methyl group was readily established by NOE and HMBC experiments. Irradiation of the H6' signal (δ6.92) resulted in NOE enhancement of the signal at δ3.94, indicating the presence of a methoxy at C5'. This assignment was supported by long range correlations from δ3.94, 6.92, and 7.12 to the carbon signal at δ157.94 in the HMBC spectrum. The relative stereochemistry around the C5-C8' axis was also determined by NOE experiments. As with korupensamine A (1), irradiation of the signals at δ1.79 (H4ax, dd, J=11.3, 17 Hz) and δ2.29 (H4eq, dd, 4.5, 17 Hz) led to enhancement of the H1' and H7' signals, respectively. Other physicochemical and spectral properties for korupensamine C include the following: [α]$_D$ −62° (C 0.54, MeOH); UV λ$_{max}$ (MeOH): 230 nm (log ε4.6), 306 (4.0), 321 (3.9), 336 (3.7); IR (film) ν$_{max}$ 3500, 2928, 1583, 1272 cm$^{-1}$; HREIMS obsd m/z 393.1975 (calc'd for C$_{24}$H$_{27}$NO$_4$, 393.1939).

Korupensamine D (4), was isomeric to korupensamine C (3), as it also provided a formula of C$_{24}$H$_{27}$NO$_4$ (m/z 393.1900). The $^1$H NMR spectrum showed features similar to those of the compounds discussed above, except for the presence of a new methyl singlet at δ2.41. This signal was attributed to an N-methyl group by HMBC and NOE experiments. Compared to those in korupensamines A–C, the signals for H1 and H3 (δ3.73 and δ2.26) appeared further upfield, supporting the assignment of an N-methyl substituent a cis-relationship of the C1 and C3 methyl substituents. The coupling constant (10.5 Hz) between the signals at δ2.20 (H4) and δ2.26 (H3) indicated that both protons were axial. However, the NOE relationships around the nitrogen ring of korupensamine D (4) were significantly different from those observed for korupensamine A–C (1–3). In contrast to korupensamines A–C, irradiation of H3 resulted in strong enhancement of the H1 signal, indicating a 1,3-diaxial relationship between them, and a cis-relationship between the methyls at C1 and C3. Irradiation of H4ax (δ2.20) led to an NOE at H7' while H4eq gave an NOE on H1'. Therefore, korupensamine D (4) had the relative stereochemistry shown in FIG. 3. Other physicochemical and spectral data for korupensamine D are as follows: [α]$_D$ +6° (C 0.3, MeOH); UV λ$_{max}$ (MeOH): 229 nm (log ε4.6), 310 (3.9), 323 (3.8), 338 (3.7); IR (film) ν$_{max}$ 3387, 3000, 1615, 1458 cm$^{-1}$; HREIMS obsd m/z 393.1900 (calc'd for C$_{24}$H$_{27}$NO$_4$, 393.1939).

In order to define the absolute configuration of the series, each of the four korupensamine A–D (1–4) was subjected to a ruthenium-mediated oxidative degradation protocol (Bringmann, et al. *Phytochemistry*, 30, 2067–2070, 1991). This procedure has been developed specifically for stereochemical determinations in this alkaloid family and employs stereo-analysis of the alanine and 3-aminobutyric acid residues produced upon degradation of the tetrahydroisoquinoline ring. This same approach has recently been employed for the determination of the absolute configuration of michellamine B (Bringmann, et al., *Angew. Chem.*, 105, 1242–1243, 1993; *Angew. Chem. Int. Ed. Engl.*, 32, 1190–1191, 1993) and extended to include the analysis of N-methyltetrahydroisoquinolines (Bringmann, et al., *Planta Med.*, 59 (suppl), 619–620, 1993).

Two different adaptations of the degradation analysis were used, depending upon the amount of compound available for study. In method I (typical procedure), a catalytic amount of RuCl$_3$•3H$_2$O and 97 mg NaIO$_4$ were added at room temperature to a solution of 9.65 mg (25 μmol) korupensamine A (1) in 0.97 mL MeCN, 0.97 mL CCl$_4$, 0.97 mL H$_2$O, and 0.97 mL aqueous phosphate buffer (pH=6). After stirring for 3 h in the dark, the phases were separated and the aqueous layer was extracted 3 times with CCl$_4$. The aqueous phase was lyophilized and the residue extracted with ultrasound assistance with 10 mL dry MeOH for 30 min followed by separation of insoluble inorganic salts by centrifugation. The ice-cooled solution was saturated with gaseous HCl for 10 min and stirred at room temperature for 24h. The solvent was evaporated, and the residue suspended in 0.5 mL of dry CH$_2$Cl$_2$ followed by addition of 0.2 mmol freshly prepared (R)-α-methoxy-α-trifluoromethylphenylacetic acid chloride ((R)-MTPA-Cl) and 60 μL of dry Et$_3$N. After stirring at room temperature for 30 min, GC analysis was performed as described earlier (Bringmann, et al., supra, 1991; Bringmann, et al., supra, 1993).

In method II (typical procedure for degradation reactions on a smaller scale in 1.5 ml-Wheaton vials), a catalytic amount of RuCl$_3$•3H$_2$O was added to a solution of 1.0 mg (2.5 μmol) korupensamine C (3) in a mixture of 50 μL MeCN, 50 μL CCl$_4$, 80 μL H$_2$O, and 50 μL aqueous phosphate buffer (pH=6). While stirring in the dark at room temperature, 20 mg NaIO$_4$ were added in portions over 30 min and stirred for another hour. For workup, the mixture was diluted with 1 mL H$_2$O and extracted 3 times with CHCl$_3$, and the aqueous phase was lyophilized with a "speed vac" concentrator until dry. The residue was extracted, with ultrasound assistance, with 5 mL of dry MeOH for 5 h followed by centrifugation of insoluble inorganic salts. Subsequent esterification of the amino acids was performed as described for method I. For the preparation of the Mosher-type derivatives, the residue of the methyl esters was suspended in 0.2 mL dry CH$_2$Cl$_2$ treated with 5 μL of dry Et$_3$N and 0.3 mL (R)-MTPA-Cl and stirred for 30 min. For GC analysis, the solvent was evaporated and the residue was dissolved in 0.5 mL dry CH$_2$Cl$_2$. The results of the degradation experiments are set forth in Table 5.

TABLE 5

| | Results of the Degradation Reactions | | |
|---|---|---|---|
| Compound | Method | Products from C1 | Products from C3 |
| 1 | I | D-alanine | R-ABA[b] |
| 2 | I | D-alanine | R-ABA |
| 3 | II | D-alanine | R-ABA |
| 4 | II[a] | D-N-methyl-alanine | S-N-methyl-ABA |
| | | D, L-alanine | S-ABA |

[a]The reaction time for the oxidation was restricted to 2½ h.
[b]ABA = 3-aminobutyric acid Accordingly, the oxidative degradation of the trans-configured alkaloids, korupensamines A–C (1–3), gave 3-(R)-aminobutyric acid and D-alanine, thus establishing these three alkaloids to be 1R,3R-configured, whereas the stereochemical analysis of the degradation products of the cis-compound, korupensamine D (4), revealed this alkaloid to be 1R,3S-configured. Given the relative configurations, as established above by $^1$H NMR, the four new alkaloids are represented by the specific stereostructures 1–4, i.e., with axial P-configuration for 1, 3, and 4, and M-configuration for 2, as shown in FIG. 1.

This definitive stereochemical assignment of the axial chirality of the korupensamines A–D was further confirmed by CD-spectroscopy. Thus, korupensamine A (1) was found to exhibit a CD-spectrum (see FIG. 4A and Table 6) nearly opposite to that of the closely related naphthyl tetrahydroisoquinoline alkaloid ancistrobrevine B (see FIG. 4B) (Bringmann, et al., supra, 1992). Similarly, the nearly opposite CD-spectra of korupensamines C and D (3 and 4), compared with that of ancistrobrevine B, as well as the nearly identical CD-spectra of korupensamine B (2) and ancistrobrevine B (see Table 6), were in full agreement with the above established absolute configurations of the biaryl axes of the new naphthyl tetrahydroisoquinoline alkaloids.

TABLE 6

A Comparison of Selected CD-data$^a$ for Korupensamines A–D and Ancistrobrevine B

| Korupensamines | | | | Ancistrobrevine |
|---|---|---|---|---|
| A (1) | B (2) | C (3) | D (4) | B |
| −120 (210.0) | +58 (212.0) | −284 (209.5) | −166 (208.5) | +157 (210.0) |
| −119 (222.5) | +44 (219.0) | −221 (224.0) | −81 (218.0) | +198 (225.0) |
| +44 (257.0) | −75 (238.0) | +66 (238.0) | +144 (235.0) | −135 (239.0) |
| +24 (248.0) | +3 (253.0) | +39 (247.0) | −7 (247.0) | |

$^a\Delta\epsilon[\text{cm}^2 \cdot \text{mol}^{-1}]$ ($\lambda_{max}[\text{nm}]$)

The korupensamines of the present invention and their dimeric derivatives, the michellamines (Manfredi, et al., supra), thus represent a new group of naphthylisoquinoline alkaloids with a C5 to C8' linkage. Interestingly, both the michellamines and the korupensamines A–D (1–4) have R configuration at C1, despite stereochemical variations at C3 and the C5-C8' axis.

Example 3

This example illustrates a procedure for the preparation of HBr salts of the korupensamines as obtained in Example 1.

A solution of korupensamine B in MeOH is treated dropwise with 9M HBr (1.1 mole equivalents). After addition is complete, the solvents are evaporated, providing the HBr salt. Other salts of the korupensamines may be prepared in a similar manner.

Example 4

Figure 5:
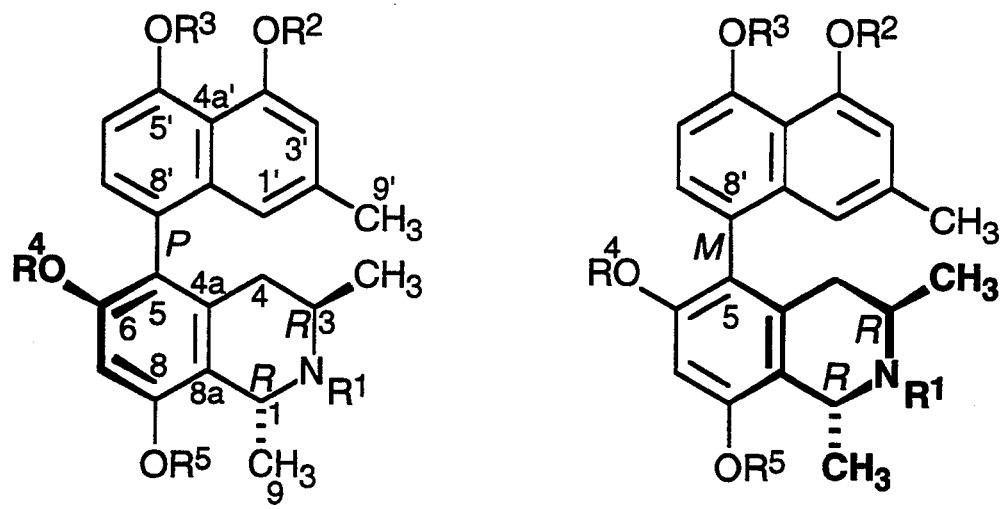
FIG. 5 more generally illustrates antimalarial korupensamines and derivatives, wherein $R^1$, $R^2$, $R^3$, $R^4$ and $R^5$ are the same or different and are each H, $C_1$-$C_6$ alkyl, $R^6CH_2$—$R^6CO$—, $R^6SO_2$—, wherein $R^6$ is $C_1$-$C_6$ alkyl or aryl, and one or more ring positions at 1', 3', 4', 5', 6', 7', 6, 7, or 8 may instead contain a halogen, nitro, amino, hydroxyl, thiol, or cyano substituent.
Figure 5:
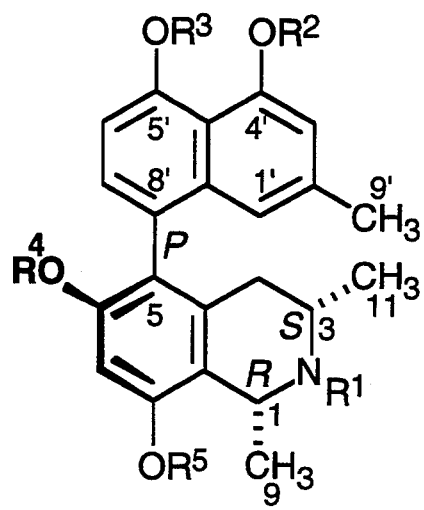

This example illustrates a procedure for the preparation of antimalarial derivatives (FIG. 5) of the korupensamines obtained in Example 1.

Using well-known organic chemical methodology, a number of structural modifications of the korupensamines can be made to provide derivatives which express in vitro and in vivo antimalarial activity; the antimalarial activity can be demonstrated as in Example 5.

Depending on the stoichiometric amount of the particular reactant, the korupensamines or derivatives thereof can be substituted at one, some, or all of the respective available positions. For example, when one of the korupensamines A, B, C or D or derivative thereof is reacted with a certain amount of CH$_3$COCl, acetate can be introduced at one, some, or all of R$^1$, R$^2$, R$^3$, R$^4$, and R$^5$.

Examples of these include, but are not limited to:

1. Conversion to ester, sulfonate ester, and ether substituents at one or more phenolic hydroxyl positions in the korupensamines or derivatives thereof (e.g., at C-4', C-5', C-6, or C-8):

For example, for preparation of esters or sulfonate esters, korupensamine A, B, C, or D can be reacted with an acid halide (RCOX or RSO$_2$X, where X=Cl, Br, or I, and R is an C$_1$-C$_6$ aliphatic or aromatic radical) in anhydrous pyridine or triethylamine. Alternatively, korupensamine A, B, C, or D may be reacted with an acid (RCO$_2$H or RSO$_3$H wherein R is an aliphatic or aromatic radical) and dicyclohexylcarbodiimide in triethylamine to prepare the ester or sulfonate ester.

For preparation of ethers, korupensamine A, B, C, or D is reacted with an organic halide (e.g., RX or RCH$_2$-X, where X=Cl, Br, or I, and R is a C$_1$-C$_6$ aliphatic or aromatic radical) in anhydrous acetone with anhydrous potassium carbonate.

For instance:

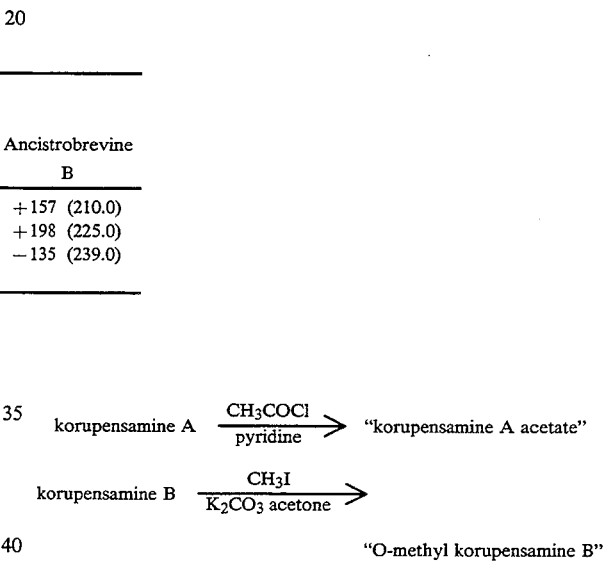

2. Removal of an ether methyl group(s) (e.g., at C-4' and/or C-5' ) to provide a phenolic hydroxyl functionality and/or conversion of that moiety to an ester, sulfonate, or other ether:

For example, for hydrolytic cleavage of the methyl ether and conversion to phenolic hydroxyl, korupensamine A, B, C, or D is reacted with BBr$_3$ or BX$_3\bullet$(CH$_3$)$_2$S in CH$_2$Cl$_2$ (where X=F, Cl, or Br). The resulting phenol can be converted to esters, sulfonate esters, or ethers as described above.

For instance:

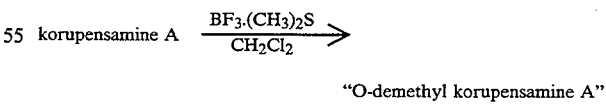

3. Preparation of amide or sulfonamide derivatives at the amine site in the korupensamines or derivatives thereof:

For example, for preparation of amide or sulfonamide derivatives, the same general procedures described above (in procedure 1) apply. In either case (procedure 1 or 3), an appropriate functional group protection strategy (blocking/deblocking of selected groups) is applied.

For instance:

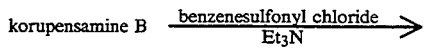

"korupensamine B benzenesulfonamide"

4. Conversion of the secondary amine functionality to an alkyl quaternary ammonium salt or to a tertiary amine:

For example, for preparation of tertiary amines, korupensamine A, B, C, or D is reacted with an aldehyde, and the resulting product is then reduced with NaBH₄.

Alternatively, for preparation of an alkyl ammonium salt, korupensamine A, B, C, or D is reacted with an alkyl halide (RX, where X=Cl, Br, or I, and R is an $C_1$-$C_6$ aliphatic radical) in anhydrous aprotic solvent.

For instance:

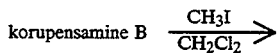

"korupensamine B dimethylammonium iodide"

5. Conversion of the tertiary amine function to a secondary amine:

For example, for preparation of a secondary amine, korupensamine D is reacted with cyanogen bromide to give korupensamine D cyanamide, which is then treated with LiAlH₄.

For instance:

N-demethyl korupensamine D

6. Conversion of one or more phenolic hydroxyl groups (e.g., at C-4', C-5', C-6, or C-8) to an aromatic hydrogen substituent:

For example, korupensamine A, B, C, or D is converted (after suitable protection of the amine function if necessary) to the triflate ester, followed by reductive deoxygenation of the triflate ester to give the corresponding 6-deoxykorupensamine.

For instance:

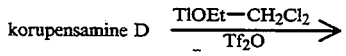

korupensamine D, triflate ester

6-deoxykorupensamine D

7. Substitution of one or more hydrogen substituents on the aryl systems (e.g., at C-1', C-3', C-4', C-5', C-6', C-7', C-6, C-7, C-8) by halogen, nitro, amino, hydroxyl, thiol, or cyano groups:

For example, for preparation of bromine-substituted derivatives, korupensamine A, B, C, or D is reacted with Br₂ in H₂O. For preparation of other substituted derivatives, korupensamine A, B, C, or D is treated with HNO₃/HOAc to provide nitro-substituted (—NO₂) derivatives. In turn, the nitro derivative can be reduced to the amino derivative. The amino-derivative is the point of origin of the chloro, iodo, cyano, thiol, and hydroxyl substitution via well-known and practiced diazonium substitution reactions.

For instance:

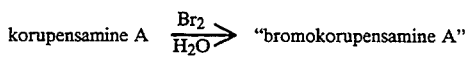

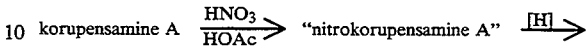

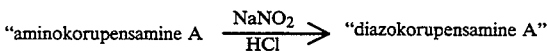

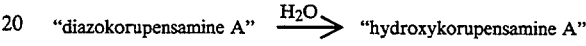

Example 5

This example illustrates the antimalarial activity of the korupensamines of the present invention. The antimalarial activity may be demonstrated both by in vitro as well as in vivo tests, as exemplified in the following. Continuous in vitro cultures of asexual erythrocytic stages of *P. falciparum* (strain NF 54/64, clone A1A9) were maintained following essentially the method of Trager and Jensen (*Science*, 193, 673–675, 1976) at 37° C. under an atmosphere of 5% $CO_2$, 5% $O_2$, and 90% $N_2$. The host cells were human erythrocytes (A or O Rh+). The culture medium was RPMI 1640 (Gibco), containing HEPES (BDH; 4.57 gL$^{-1}$) glucose (Sigma; 1.54 gL$^{-1}$), 5% NaHCO₃ (Merck; 34.78 mlL$^{-1}$), and gentamycin (Merck; 8.70 mlL$^{-1}$) supplemented with 10% human plasma (A Rh+). Parasites were subinoculated every 3–4 days with initial conditions of 1% parasitemia and 1% hematocrit.

In vitro testing with *P. falciparum* was as follows. Each compound was dissolved in DMSO at a concentration of 20 mg ml$^{-1}$. These solutions were further diluted with physiological saline to obtain a stock solution of 500 μg ml$^{-1}$. Each test substance was applied in a series of seven, 4-fold dilutions (maximum concentrations 50 or 5 μg ml$^{-1}$). Each compound was tested in 6-fold repeats. Chloroquine was tested similarly, as a positive control.

The test protocol was performed in vitro, based upon the method of Desjardins, et al. (*Antimicrobial Agents Chemother.*, 16, 710–718, 1979). The parasites (200 μl of a suspension with initial parasitemia of 0.5% and hematocrit of 1.5%) were incubated for 24 h in microtiter plates (Falcon MicroTest III) in hypoxanthine-free medium in the presence of 25 μl of test solution. The plates contained a negative control (6 wells with non-parasitized RBCs, no drug) and a positive control (6 wells with parasitized RBCs no drug). Thereafter, 25 μl of ³H-hypoxanthine solution (Amersham) was added (0.5 μCi well$^{-1}$), and the parasites were incubated for a further period of 18 h. Each well was harvested with a Cell Harvester (Nunc). The filter papers were dried for 2 h at 52° C. and their radioactivity was measured by liquid scintillation counting in Optiscint HiSafe (LKB Pharmacia).

The mean results, obtained as counts per min (cpm), were expressed as percentages of incorporation or growth inhibition. The sigmoid dose-response curve was then linearized by probit analysis with the aid of software provided by IWONL (Gent), adapted by G. Timperman and used to derive the $IC_{50}$ values.

In the case of tests using *P. berghei* (Anka strain), the parasites were maintained and were incubated in the same conditions as for *P. falciparum* (above) except that the incubations were started immediately in the presence of the $^3$H-hypoxanthine and for 24 hour total duration (i.e., no delay in the addition of the $^3$H-hypoxanthine). As before, the incorporated radioactivity was used as a measure for parasite growth. The in vitro antimalarial activity of korupensamines is illustrated by korupensamines A and B against *P. falciparum* and *P. berghei* in Table 7 below.

TABLE 7

$IC_{50}$ Values (averages of 6 repeat tests) for korupensamine A and korupensamine B obtained with *Plasmodium falciparum* (NP54/64, clone A1A9) and *Plasmodium berghei* (Anka) in vitro

| Korupensamine | $IC_{50}$ *P. faciparum* ($\mu$g ml$^{-1}$) | $IC_{50}$ *P. berghei* ($\mu$g ml$^{-1}$) |
| --- | --- | --- |
| A | 0.307 | 0.555 |
| B | 0.175 | 0.490 |

The korupensamines can also be shown to have in vive antimalarial activity. For example, korupensamine A was tested in vive as follows.

Outbred, female, six-week-old OF1 mice (six mice per group treated and nontreated [control]) were inoculated intraperitoneally on day 0 with $10^6$ *P. berghei* (Anka strain) blood forms. Two hours later, they were administered orally 50 mg/kg of korupensamine A. A second, third, and fourth treatment (50 mg/kg each) was given after 24, 48, and 72 h respectively (days 1, 2, and 3). A microscopic examination of the relative extent of the in vive parasitemia, performed from blood smears after 4 days, revealed a marked inhibition of the development of *P. berghei* erythrocytic forms. The parasitemia (%) in the control (not drug treated) group was 2.45 (range 2.21–2.69; N=6) compared to 0.69 (range 0.48–0.91; N=6) for the treated group.

Example 6

This example illustrates various possible pharmaceutical compositions which include the antimalarial compounds of the present invention.

The compounds of the present invention may be made into pharmaceutical compositions by combination with appropriate pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective routes of administration.

The compounds can be used singularly alone, in combination with each other, or in combination with other antimalarial agents. When mammals infected with malaria parasites are being treated, at least one compound of the present invention can be co-administered with chloroquine or other antimalarial agent(s) such as mefloquine, halofantrine, artemisinin, artemether, pyrimethamine, or quinine.

The following methods and excipients are merely exemplary and are in no way limiting:

In pharmaceutical dosage forms, the compounds of the present invention may be used in the form of their pharmaceutically acceptable salts and also may be used alone or in appropriate association, as well as in combination, with other pharmaceutically active compounds.

In the case of oral preparations, the compounds of the present invention may be used alone or in combination with appropriate additives to make tablets, powders, granules, or capsules, e.g., with conventional additives such as lactose, mannitol, corn starch, or potato starch; with binders such as crystalline cellulose, cellulose derivatives, acacia, corn starch, or gelatins; with disintegrators such as corn starch, potato starch, or sodium carboxymethylcellulose; with lubricants such as talc or magnesium stearate; and, if desired, with diluents, buffering agents, moistening agents, preservatives, and flavoring agents.

The compounds of the present invention may be formulated into preparations for injections by dissolving, suspending, or emulsifying them in an aqueous or nonaqueous solvent, such as vegetable or other similar oils, synthetic aliphatic acid glycerides, esters of higher aliphatic acids, or propylene glycol; and, if desired, with conventional additives such as solubilizers, isotonic agents, suspending agents, emulsifying agents, stabilizers and preservatives.

The compounds of the present invention can be utilized in aerosol formulation to be administered via inhalation. The compounds of the present invention can be formulated into pressurized acceptable propellants such as dichlorodifluoromethane, propane, nitrogen, and the like.

Furthermore, the compounds of the present invention may be made into suppositories by mixing with a variety of bases such as emulsifying bases or water-soluble bases. The compounds of the present invention can be administered rectally via a suppository. The suppository can include vehicles such as cocoa butter, carbowaxes, and polyethylene glycols, which melt at body temperature, yet are solid at room temperature.

Unit dosage forms for oral or rectal administration such as syrups, elixirs, suspensions and suppositories may be provided wherein each dosage unit, e.g., teaspoonful, tablespoonful, tablet, or suppository contains a predetermined amount of the composition containing at least one compound of the present invention; similarly, unit dosage forms for injection or intravenous administration may comprise a korupensamine or korupensamine derivative composition as a solution in sterile water, normal saline, or other pharmaceutically acceptably carrier.

The term "unit dosage form" as used herein refers to physically discrete units suitable as unitary dosages for human and animal subjects, each unit containing a predetermined quantity of at least one compound of the present invention calculated in an amount sufficient to produce the desired effect in association with a pharmaceutically acceptable diluent, carrier, or vehicle. The specifications for the novel unit dosage forms of the present invention depend on the particular compound employed and the effect to be achieved, as well as the pharmacodynamics associated with each compound in the particular host.

The pharmaceutically acceptable excipients, for example, vehicles, adjuvants, carriers, or diluents, are readily available to the public.

One skilled in the art can determine easily the appropriate method of administration for the precise formulation of the composition being used. Any necessary adjustments in dose can be made readily to meet the nature or severity of the infection and adjusted accordingly by the skilled practitioner.

EXAMPLE 7

This example illustrates various possible uses of the antimalarial korupensamines and korupensamine derivatives of the present invention in the treatment or prevention of malarial infections.

An antimalarial effective amount of at least one compound of the present invention can be administered to a mammal, particularly a human, to treat or prevent malarial infections. An antimalarial effective amount is defined as that amount of compound required to be administered to an individual recipient mammal to achieve an antimalarial effective blood and/or tissue level to inhibit the parasite. The antimalarial effective blood level might be chosen, for example, to inhibit Plasmodia parasites in an in vitro screening assay. Alternatively, the antimalarial effective blood level can be defined as that concentration which demonstrably inhibits the presence, viability, or reproduction of the parasite in the recipient mammal's blood, or which renders the mammal asymptomatic to the particular malarial infection. Since a target antimalarial effective blood level is used as the preferred endpoint for dosing, the actual dose and schedule for drug administration for each particular recipient mammal will vary depending upon interindividual differences in the pharmacokinetics, drug disposition, and metabolism of the particular compound selected for use. Moreover, the dose may vary when the compounds are used prophylactically or when used in combination with other drugs.

Such dosage amounts can be readily ascertained without undue burden and experimentation by those skilled in the art. As an example of an antimalarial effective amount, the daily dosage for a particular recipient mammal can range from about between 0.01 mg/kg body weight to 100 mg/kg body weight, depending upon the particular korupensamine or derivative thereof selected for use.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred products and methods may be used and that it is intended that the invention may be practiced otherwise than as specifically described herein. Accordingly, this invention includes all modifications encompassed within the spirit and scope of the invention as defined by the following claims.

What is claimed is:

1. A substantially pure compound having the formula:

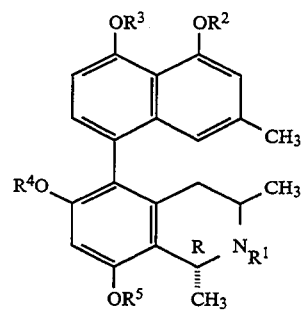

wherein $R^1$, $R^2$, $R^3$, $R^4$ and $R^5$ are the same or different and are each H, $C_1$-$C_6$ alkyl $R^6CH_2-$, $R^6CO-$, or $R^6SO_2-$ wherein $R^6$ is H, $C_1$-$C_6$ alkyl or aryl, and one or more ring positions at 1', 3', 4', 5', 6', 7', 6, 7 or 8 may instead be a halogen, nitro, amino, hydroxyl, thiol, or cyano substituent, or a pharmacologically acceptable salt thereof.

2. The compound of claim 1, wherein said compound has the formula

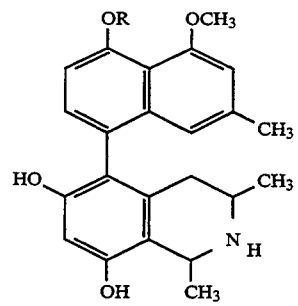

wherein R is either H or $CH_3$, or a pharmacologically acceptable salt thereof.

3. The compound of claim 2, wherein said compound is korupensamine A, B, C, or D, or a pharmacologically acceptable salt thereof.

4. The compound of claim 3, wherein said compound is korupensamine A, B, C, or D.

5. The compound of claim 1, wherein said compound is selected from the group consisting of

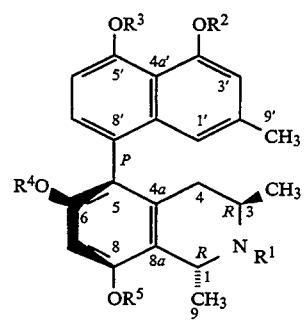

-continued

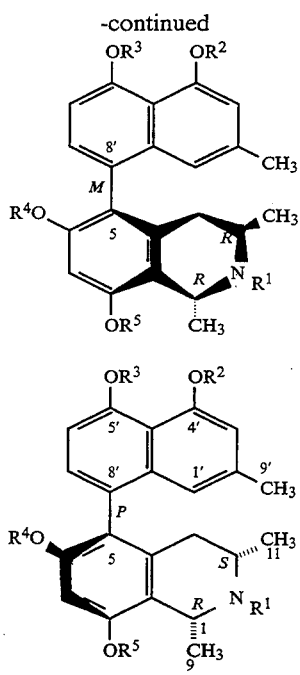

wherein $R^1$, $R^2$, $R^3$, $R^4$ and $R^5$ are the same or different and are each H, $C_1$-$C_6$ alkyl, $R^6CH_2$—, $R^6CO$—, or $R^6SO_2$— wherein $R^6$ is H, $C_1$-$C_6$ alkyl or aryl, and one or more ring positions at 1', 3', 4', 5', 6', 7', 6, 7 or 8 may instead be a halogen, nitro, amino, hydroxyl, thiol, or cyano substituent, or a pharmacologically acceptable salt thereof.

6. A pharmaceutical composition which comprises a pharmaceutically acceptable carrier and an antimalarial effective amount of at least one compound according to claim 1.

7. The pharmaceutical composition of claim 6, which composition further comprises an antimalarial effective amount of chloroquine, mefloquine, halofantrine, artemisinin, artemether, pyrimethamine, or quinine.

8. A pharmaceutical composition which comprises a pharmaceutically acceptable carrier and an antimalarial effective amount of at least one compound according to claim 2.

9. The pharmaceutical composition of claim 8, which composition further comprises an antimalarial effective amount of chloroquine, mefloquine, halofantrine, artemisinin, artemether, pyrimethamine, or quinine.

10. A pharmaceutical composition which comprises a pharmaceutically acceptable carrier and an antimalarial effective amount of at least one compound according to claim 3.

11. The pharmaceutical composition of claim 10, which composition further comprises an antimalarial effective amount of chloroquine, mefloquine, halofantrine, artemisinin, artemether, pyrimethamine, or quinine.

12. A pharmaceutical composition which comprises a pharmaceutically acceptable carrier and an antimalarial effective amount of at least one compound according to claim 4.

13. The pharmaceutical composition of claim 12, which composition further comprises an antimalarial effective amount of chloroquine, mefloquine, halofantrine, artemisinin, artemether, pyrimethamine, or quinine.

14. A pharmaceutical composition which comprises a pharmaceutically acceptable carrier and an antimalarial effective amount of at least one compound according to claim 5.

15. The pharmaceutical composition of claim 14, which composition further comprises an antimalarial effective amount of chloroquine, mefloquine, halofantrine, artemisinin, artemether, pyrimethamine, or quinine.

16. A method of isolating and purifying a compound of claim 1 from *Ancistrocladus korupensis*, which method comprises the steps of:
    (a) extracting dried plant material with an organic solvent to obtain a crude extract,
    (b) acid-base partitioning said crude extract to obtain a crude organic base fraction,
    (c) subjecting said crude organic base fraction to centrifugal partition chromatography, and
    (d) isolating said compounds with an amino-bonded phase HPLC column.

17. A method of treating or preventing a malarial infection which comprises administering to a mammal in need thereof an antimalarial effective amount of at least one compound according to claim 1.

18. The method of claim 17, which method further comprises co-administering an antimalarial effective amount of chloroquine, mefloquine, halofantrine, artemisinin, artemether, pyrimethamine, or quinine.

19. The method of claim 17, wherein said infection is by a Plasmodium sp. parasite.

20. The method of claim 19, wherein said parasite is *P. falciparum, P. vivax, P. malariae, P. ovale* or *P. berghei*.

21. The method of claim 17, wherein said mammal is a human.

22. A method of treating or preventing a malarial infection which comprises administering to a patient in need thereof an antimalarial effective amount of at least one compound according to claim 2.

23. The method of claim 22, which method further comprises co-administering an antimalarial effective amount of chloroquine, mefloquine, halofantrine, artemisinin, artemether, pyrimethamine, or quinine.

24. The method of claim 22, wherein said infection is by a Plasmodium sp. parasite.

25. The method of claim 24, wherein said parasite is *P. falciparum, P. Vivax, P. malariae, P. ovale* or *P. berghei*.

26. The method of claim 22, wherein said mammal is a human.

27. A method of treating or preventing a malarial infection which comprises administering to a patient in need thereof an antimalarial effective amount of at least one compound according to claim 3.

28. The method of claim 27, which method further comprises co-administering an antimalarial effective amount of chloroquine, mefloquine, halofantrine, artemisinin, artemether, pyrimethamine, or quinine.

29. The method of claim 27, wherein said infection is by a Plasmodium sp. parasite.

30. The method of claim 29, wherein said parasite is *P. falciparum, P. Vivax, P. malariae, P. ovale* or *P. berghei*.

31. The method of claim 27, wherein said mammal is a human.

32. A method of treating or preventing a malarial infection which comprises administering to a patient in need thereof an antimalarial effective amount of at least one compound according to claim 4.

33. The method of claim 32, which method further comprises co-administering an antimalarial effective amount of chloroquine, mefloquine, halofantrine, artemisinin, artemether, pyrimethamine, or quinine.

34. The method of claim 32, wherein said infection is by a Plasmodium sp. parasite.

35. The method of claim 34, wherein said parasite is *P. falciparum, P. Vivax, P. malariae, P. ovale* or *P. berghei.*

36. The method of claim 32, wherein said mammal is a human.

37. A method of treating or preventing a malarial infection which comprises administering to a patient in need thereof an antimalarial effective amount of at least one compound according to claim 5.

38. The method of claim 37, which method further comprises co-administering an antimalarial effective amount of chloroquine, mefloquine, halofantrine, artemisinin, artemether, pyrimethamine, or quinine.

39. The method of claim 37, wherein said infection is by a Plasmodium sp. parasite.

40. The method of claim 39, wherein said parasite is *P. falciparum, P. Vivax, P. malariae, P. ovale* or *P. berghei.*

41. The method of claim 37, wherein said mammal is a human.

* * * * *

UNITED STATES PATENT AND TRADEMARK OFFICE
CERTIFICATE OF CORRECTION

PATENT NO. : 5,409,938

DATED : APRIL 25, 1995

INVENTOR(S) : MICHAEL R. BOYD, GUIDO FRANCOIS, GERHARD BRINGMANN, YALI F. HALLOCK, KIRK P. MANFREDI AND JOHN H. CARDELLINA II

It is certified that error appears in the above-identified patent and that said Letters Patent is hereby corrected as shown below:

ON THE TITLE PAGE:

[75] Inventors: fourth inventor, "Yaii F. Hallock" should read -- Yali F. Hallock --.

Signed and Sealed this

Fifteenth Day of August, 1995

Attest:

BRUCE LEHMAN

Attesting Officer     Commissioner of Patents and Trademarks